United States Patent [19]

Koshinaka et al.

[11] Patent Number: 5,008,558

[45] Date of Patent: Apr. 16, 1991

[54] SYSTEM FOR DETECTING MINUTE PARTICLES ON OR ABOVE A SUBSTRATE

[75] Inventors: Masao Koshinaka; Minoru Akiyama; Hitoshi Tanaka; Toshimasa Tomoda, all of Hyogo, Japan

[73] Assignee: Mitsubishi Denki Kabushiki Kaisha, Tokyo, Japan

[21] Appl. No.: 373,801

[22] Filed: Jun. 29, 1989

[30] Foreign Application Priority Data

Oct. 12, 1988 [JP] Japan ................... 63-257780

[51] Int. Cl.$^5$ ........................... G01N 21/88
[52] U.S. Cl. ..................... 250/563; 250/571; 356/431
[58] Field of Search ............ 250/571, 572, 562, 563, 250/234, 235, 236; 356/335, 336, 430, 431, 445, 446, 338, 339, 340, 341, 342

[56] References Cited

U.S. PATENT DOCUMENTS

| | | | |
|---|---|---|---|
| 4,376,583 | 3/1983 | Alford et al. | 356/237 |
| 4,468,120 | 8/1984 | Tanimoto et al. | 356/237 |
| 4,689,491 | 8/1987 | Lindow et al. | 250/572 |

FOREIGN PATENT DOCUMENTS 63-30570 6/1988 Japan .

OTHER PUBLICATIONS

General Scanning, Inc., *General Scanning* brochure GS130150 (General Scanning Inc., Watertown, MA, 1984, pp. 3–12).

"SiO$_2$ Particulates Dispersed in CVD Reactor" A. Shintani et al., J. Electro Chm. Soc. vol. 124 No. 11 (1977) 1771.

*Primary Examiner*—David C. Nelms
*Attorney, Agent, or Firm*—Wolf, Greenfield & Sacks

[57] ABSTRACT

A fine-particle measuring apparatus designed to measure fine particles attached to the surface of a substrate for a semiconductor device set in a processing unit for formation of films, etching, cleaning, etc. and fine particles suspended in the space above the substrate surface by the use of scattering of a laser beam caused by these fine particles. The measuring apparatus comprises a laser beam scanning mechanism for irradiating a measuring space with a laser beam the angular position of which is minutely modulated at a predetermined frequency, a photodetector which receives light scattered by a fine particle and converts the received light into an electrical signal, and a signal processor which extracts from the electrical signal output by the photodetector a signal component whose frequency is the same as or double that of a modulating signal for the minute scanning with the laser beam and which has a constant phase difference in terms of time with respect to the modulating signal. Thus, it is possible to measure fine particles with high sensitivity without substantially disturbing the environment inside the process unit or the process itself.

7 Claims, 7 Drawing Sheets

INCIDENT ANGLE $\varphi$

SYSTEM FOR DETECTING MINUTE PARTICLES ON OR ABOVE A SUBSTRATE

BACKGROUND OF THE INVENTION

1. Field of the Invention

The present invention relates to measurement of fine particles (foreign matter) present in a process unit for formation of films, etching, cleaning, etc.

2. Description of the Prior Art

Figure 7:
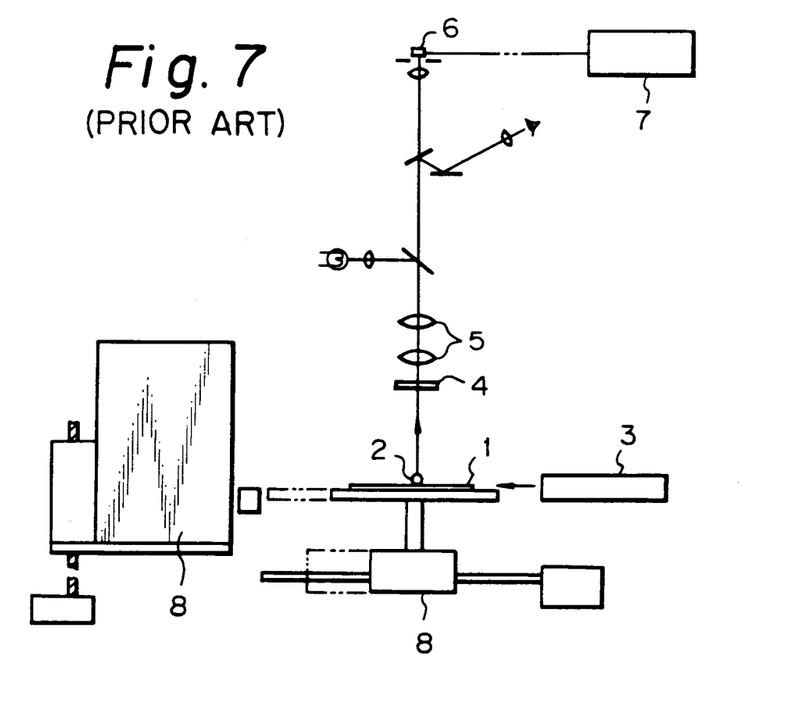
FIGS. 7 and 8 show the arrangements of conventional fine-particle measuring apparatuses, respectively.

FIG. 7 shows the arrangement of a conventional fine-particle measuring apparatus disclosed, for example, in Japanese Patent Post-Exam Publication Number 63-30570 (1988). The apparatus is designed to measure fine particles attached to the surface of a wafer. In the figure, reference numeral 1 denotes a substrate for a semiconductor device, that is, a wafer, which is an object of measurement, 2 a fine particle, 3 a laser light source (a light source for generating parallel rays), 4 a polarizer, 5 objective lenses, 6 a photodetector which converts light into an electric signal, and 7 an electronic circuit device which processes information output from the photodetector 6 to obtain the results of measurement of fine particles. The reference numeral 8 denotes a driving mechanism for moving the position of the wafer 1.

The operation of the prior art will next be explained. Laser light emitted from the laser light source 3 is applied parallel to the surface of the wafer 1. As the laser light that is applied to the wafer surface, S-polarized laser light is employed. The S-polarized laser light is scattered by the fine particle 2. However, since the surface of the fine particle 2 has minute irregularities, the scattered light contains a large amount of P-polarized light component. On the other hand, the medium that constitutes the measuring atmosphere is usually a gas, m i.e., air, and light that is scattered by gas molecules in the manner of Rayleigh scattering contains no P-polarized light component. Accordingly, the scattered light caused by gas molecules is cut off by the polarizer 4 disposed in such a manner as to intercept the S-polarized light component. As a result, only the P-polarized light component of the scattered light from the fine particle 2 is received by the photodetector 6, and the result of measurement is obtained in the electronic circuit device 7. The driving mechanism 8 is provided to measure the distribution of fine particles on the wafer surface.

The above-described prior art suffers, however, from the following problems. The fine particle under measurement should not have on its surface minute irregularities which are regarded as much smaller than the wavelength of the laser light, and it is difficult with the prior art to measure fine particles which have relatively smooth surfaces and fine particles which have relatively small particle diameters. These fine particles may be measured by the use of P-polarized laser light or non-polarized laser light in place of S-polarized laser light. In such a case, however, the Rayleigh-scattered light (P-polarized light) scattered by the gas that constitutes the measuring atmosphere cannot be cut off with the polarizer 4, and the S/N ratio cannot therefore be increased. Thus, it is difficult with the prior art to measure fine particles having small diameters. In addition, since this prior art apparatus is not adapted to measure fine particles in a process unit but is designed for off-line inspection, it is difficult to apply the prior art apparatus to measurement of fine particles in a process unit even if the polarizer 4 and the objective lenses 5 (constituting in combination a microscope) are disposed in close proximity to the wafer 1 to limit the observation zone.

Figure 8:
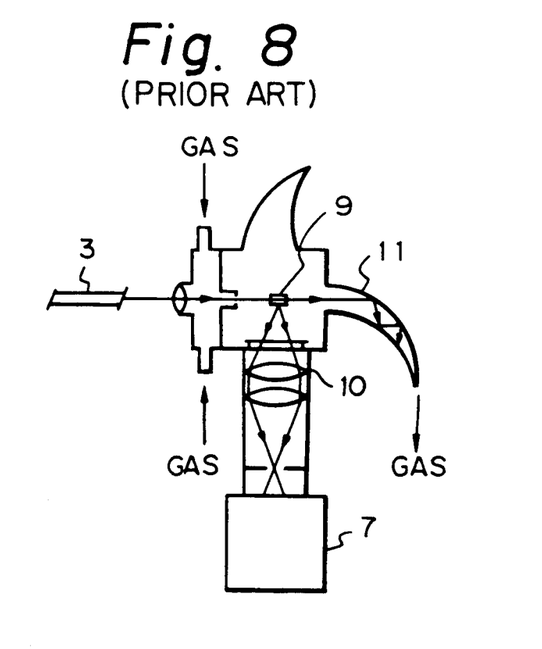

FIG. 8 is a sectional view showing the arrangement of another conventional fine-particle measuring apparatus disclosed, for example, in A. Shintani et al.: J. Electrochem. Soc. 124, No. 11 (1977), pp. 1771-1776. In the figure, the reference numeral 3 denotes a laser light source, 9 a measuring zone which is spatially limited by a light-receiving lens system 10 and which contains fine particles to be measured, 7 a photodetector, and 11 an optical trap for minimizing stray light in the measuring apparatus. In use, this prior art apparatus is connected to a process unit by the use of capillary (tube) adapted to suck in a gas containing fine particles dispersed in the process unit, thereby indirectly measuring the fine particles in the process unit.

Accordingly, this prior art involves the problem that it is impossible to measure fine particles on the surface of a wafer set in the process unit and, with regard to the fine particles suspended in the process unit, it is only possible to measure those which can be successfully sucked and transported into the measuring apparatus.

Figure 9A:
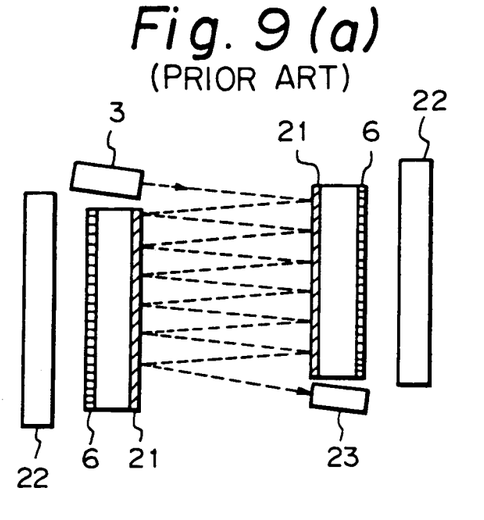
FIGS. 9(a) and 9(b) are plan and front views, respectively, of another conventional fine-particle measuring apparatus, which show the operating principle of the prior art.
Figure 9B:
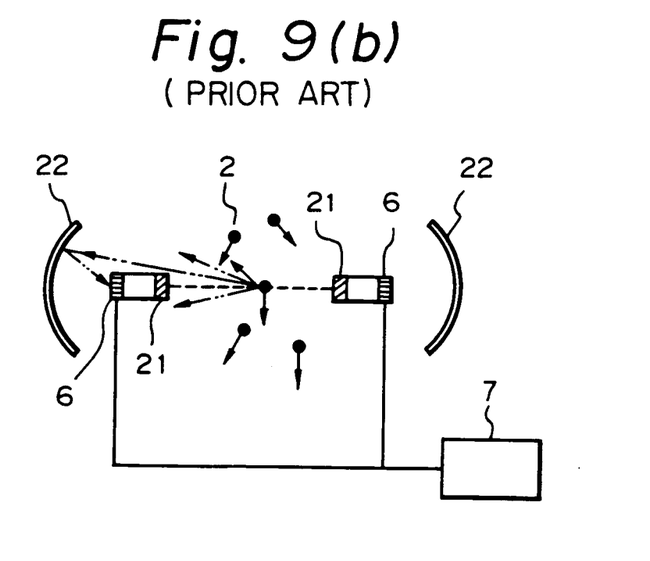

FIGS. 9(a) and 9(b) are plan and front views showing the operation of PM-100 In-Situ Particle Flux Monitor, a product available from High Yield Technology. Laser light from a laser 3 is reflected a large number of times between a pair of mirrors 21 disposed parallel to each other, thereby enlarging the two-dimensional observation zone. When fine particles 2 are passing through the zone, light is scattered thereby and this scattered light is received by a photo-detector 6 to thereby measure fine particles. It should be noted that the reference numeral 22 denotes reflecting condensers, while the numeral 23 denotes a beam stopper. This apparatus is used within a process unit.

Accordingly, this prior art is capable of measuring suspended fine particles but cannot measure those attached to the wafer surface. In addition, since the optical system (comprising the laser light source 3, the mirrors 21, the photodetector 6, etc.) is installed inside a process unit, in the case, for example, of a film forming process by atmospheric pressure thermal CVD, it is difficult to measure fine particles on the surface of the wafer heated at high temperature or those which are suspended above the wafer surface during a film forming process. Even when no film is being formed, the presence of the apparatus also causes substantial changes in the environment (e.g., the gas flow, temperature distribution, etc.) in the vicinity of the wafer. In an etching or cleaning process also, it is difficult to effect measurement without causing critical disturbances. In addition, since the measuring system according to this prior art has no means for eliminating signals (i.e., background noise) caused by light that is scattered by gas molecules constituting the measuring atmosphere medium in the manner of Rayleigh scattering, it is difficult to measure fine particles having such small particle diameters that the intensity of light scattered thereby is too weak to ensure that the desired signal will not be obscured by the background noise.

SUMMARY OF THE INVENTION

In view of the above-described problems of the prior art, it is a primary object of the present invention to provide a fine-particle measuring apparatus which is capable of measuring fine particles attached to the surface of a wafer set in a process unit for formation of films, etching, cleaning, etc. as well as fine particles suspended in the space above the wafer surface without substantially disturbing the environment inside the process unit or the process itself.

To this end, the present invention provides a fine-particle measuring apparatus designed to measure fine particles attached to the surface of a substrate for a semiconductor device and fine particles suspended in the space above the surface of the substrate by utilizing the scattering of a laser beam caused by these fine particles, comprising: a laser beam scanning mechanism for irradiating a measuring space with a laser beam the angular position of which is minutely modulated at a predetermined frequency; a photodetector which receives light scattered by any of the fine particles and converts the received light into an electrical signal; and a signal processor which extracts from the electrical signal output by the photodetector a signal component whose frequency is the same as or double that of a modulating signal for the minute scanning with the laser beam and which has a constant phase difference in terms of time with respect to the modulating signal.

According to another aspect of the present invention, the laser beam scanning mechanism effects scanning with a laser beam the angular position of which is minutely modulated at a predetermined frequency and which is superposed on an angular position scanning the speed of which can be regarded as quasi-static in comparison with the modulation.

Thus, the fine-particle measuring apparatus according to the present invention is arranged to irradiate fine particles with a laser beam while minutely modulating the angular position thereof, convert light including light scattered by any of the fine particles into an electrical signal in the photodetector, and extract from the electrical signal output by the photodetector a signal component whose frequency is the same as or double that of a modulating signal for the minute scanning with the laser beams and which has a constant phase difference in terms of time with respect to the modulating signal, that is, a signal component corresponding to the laser beam scattered by fine particles. It is therefore possible to eliminate the electrical signal component corresponding to stray light, that is, light other than the light resulting from the laser beam and the electrical signal component corresponding to the laser beam that is scattered by the gas constituting the measuring atmosphere in the manner of Rayleigh scattering as long as the medium constituting the measuring atmosphere can be regarded as homogeneous at least within the width of oscillation of minute scanning. Thus, the measuring apparatus of the present invention enables measurement of fine particles while satisfactorily reducing causes of disturbance of the measurement.

Further, it is possible to measure at least a one-dimensional distribution of fine particles present in the measuring zone by employing a laser beam scanning mechanism that effects scanning with a laser beam the angular position of which is minutely modulated at a predetermined frequency and which is superposed on an angular position scanning the speed of which can be regarded as quasi-static in comparison with the modulation.

BRIEF DESCRIPTION OF THE DRAWINGS

The above and other objects, features and advantages of the present invention will become more apparent from the following description of the preferred embodiments thereof, taken in conjunction with the accompanying drawings, in which like reference numerals denote like elements, and of which.

DESCRIPTION OF THE PREFERRED EMBODIMENTS

One embodiment of the present invention will be described below with reference to the accompanying drawings.

Figure 1:
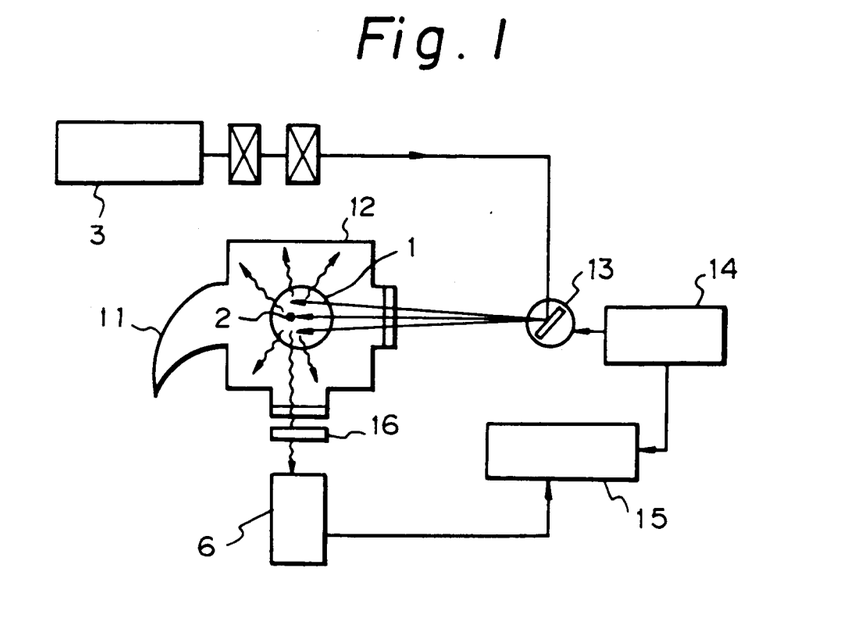
FIG. 1 shows the arrangement of one embodiment of the fine-particle measuring apparatus according to the present invention.

Referring to FIG. 1, the reference numeral 1 denotes a substrate for a semiconductor device, that is, a wafer, which is set in a process unit 12, 2 a fine particle attached to the surface of the wafer 1, 3 a laser light source, 13 a laser beam scanning mechanism for irradiating the surface of the wafer 1 with a laser beam the angular position of which is minutely modulated at a predetermined frequency, for example, a galvanometer scanner, 14 a controller attached to the scanning mechanism 13 (e.g., a galvanometer scanner such as available from General Scanning, Inc., Watertown, Mass.) to control the operation thereof, 6 a photodetector, for example, a photomultiplier, 15 a signal processor, for example, a lock-in amplifier, for extracting from an electrical signal output from the photodetector 6 a signal component whose frequency is the same as (or double) that of a modulating signal for minute scanning with the laser beam and which has a constant phase difference in terms of time with respect to the modulating signal, 16 a narrow-band pass multilayer interference filter for limiting the observation zone that contains fine particles, and 11 an optical trap for minimizing stray light in the process unit 12.

Figure 2A:
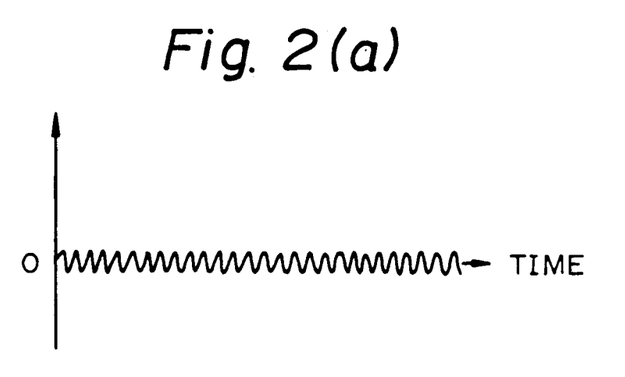
FIGS. 2(a) to 2(c) are waveform charts respectively showing a minute scanning signal, an angular position scanning signal and a superposed signal, which are used to effect scanning with a laser beam.

The operation of this embodiment will next be explained. Laser light emitted from the laser light source 3 is applied to the surface of the wafer 1 while the angular position thereof is being minutely modulated at a predetermined frequency by the operation of the scanning mechanism 13 controlled by the controller 14 that generates a modulating signal such as that shown in FIG. 2(a). At this time, when the minute scanning spot of the laser beam and the position of the fine particle 2 are coincident with each other on the surface of the wafer 1, the intensity of the scattered light reaches a maximum, whereas, when the fine particle 2 is not irradiated with the laser beam, the intensity of the scattered light is zero, as will be clear from FIGS. 3(a) to 3(d). The photodetector 6 outputs an electrical signal which comprises the following three signal components superposed one upon another, that is, an electrical signal component corresponding to the intensity of the scattered light, an electrical signal component corresponding to stray light, that is, light other than the light resulting from the laser beam (e.g., room illuminating light that undesirably enters the process unit), and an electrical signal component corresponding to the laser beam that is scattered by the gas constituting the measuring atmosphere in the process unit in the manner of Rayleigh scattering. Among the three signal components, the second one that corresponds to stray light has no correlation with the modulating signal and the third one that corresponds to the gas constituting the measuring atmosphere has no component which is synchronous with the modulating signal as long as the gas constituting the measuring atmosphere can be regarded as homogeneous at least within the width of oscillation of minute scanning. Accordingly, a signal component whose frequency is the same as that of the modulating signal for minute scanning with the laser beam (the frequency of the signal component may be double that of the modulating signal in the case where the fine particle 2 is in the vicinity of the center of the laser minute scanning range, as shown in FIG. 3) and which has a constant phase difference in terms of time with respect to the modulating signal is extracted from the electrical signal output from the photodetector 6, thereby eliminating the electrical signal component corresponding to stray light, that is, light other than the light resulting from the laser beam and the electrical signal component corresponding to the laser beam that is scattered by the gas constituting the measuring atmosphere in the manner of Rayleigh scattering, and thus enabling measurement of only the electrical signal component corresponding to the intensity of light scattered by the fine particle 2. It is therefore possible to accurately measure fine particles having smaller diameters than in the case of the prior art.

Figure 4:
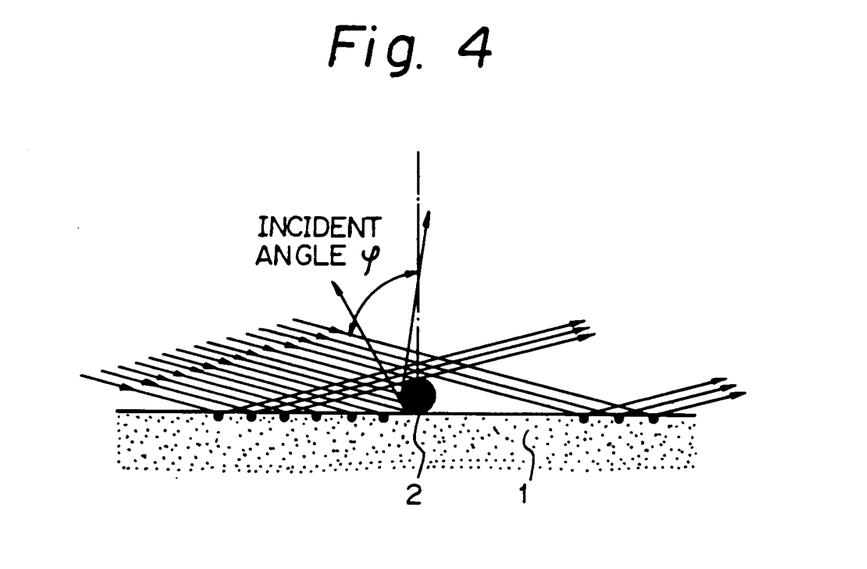
FIG. 4 shows the angle at which the laser beam is irradiated.

Since the intensity of light scattered by the fine particle 2 is proportional to the intensity of the laser beam, an effective way of improving the measuring capacity is to increase the intensity of the irradiating laser beam. However, if the intensity is excessively high, the surface of the wafer 1 may be damaged. Therefore, the laser beam is applied to the wafer surface at a relatively large angle of incidence, as shown in FIG. 4, thereby enabling a lowering of the intensity of the laser beam with respect to the surface of the wafer 1 without any change in the intensity with respect to the fine particle 2.

Figure 5:
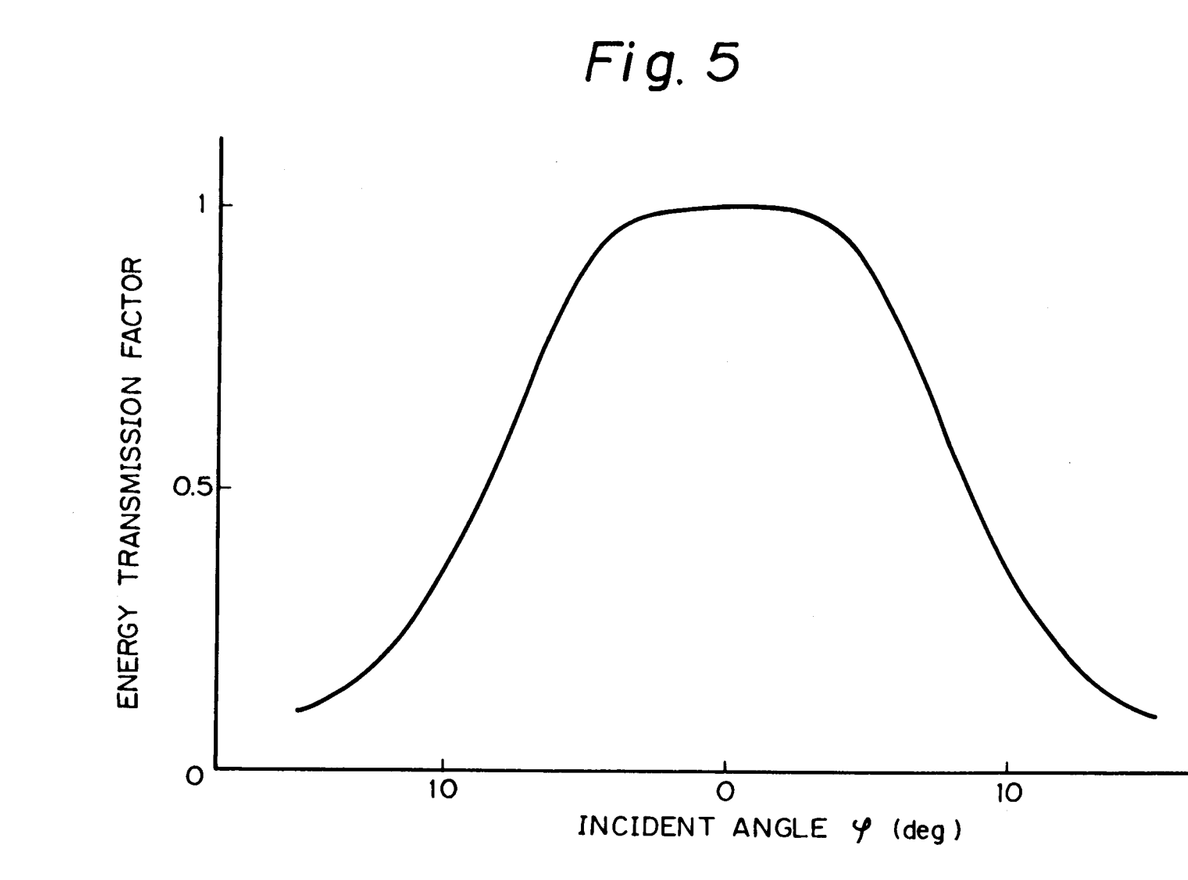
FIG. 5 is a characteristic chart showing the incident angle dependence of the transmission factor of an interference filter.

FIG. 5 shows the results of calculation of the incident angle dependence of the energy transmission factor with respect to light having a wavelength of 488 nm in the case of a multilayer interference filter used by way of example, the filter having a center transmission frequency of 488 nm and the following structure:

$$n_a/(LH)^3 2L(HL)^3/n_s$$

wherein

H: $n = 2.35$ (ZnS)

L: $n = 1.38$ (M$_g$F$_2$)

wafer: $n = 1.52$ (BK7)

It will be understood from the figure that, as the incident angle $\phi$ increases, the transmission factor decreases, thus limiting the visual field. Therefore, by disposing a narrow-band pass multilayer interference filter 16 having the same center transmission wavelength as that of the laser beam employed in front of the photodetector 6 as shown in FIG. 1, it is possible to limit the observation zone viewed from the photodetector 6 and hence reduce the influence on the measurement of the stray light in the process unit 12 resulting from the laser beam.

Figure 2B:
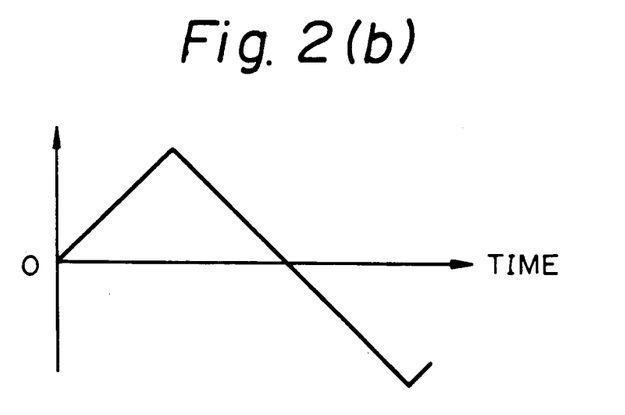
Figure 2C:
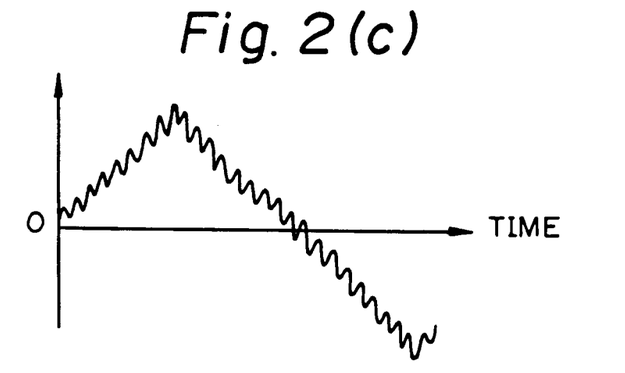
Figure 3A:
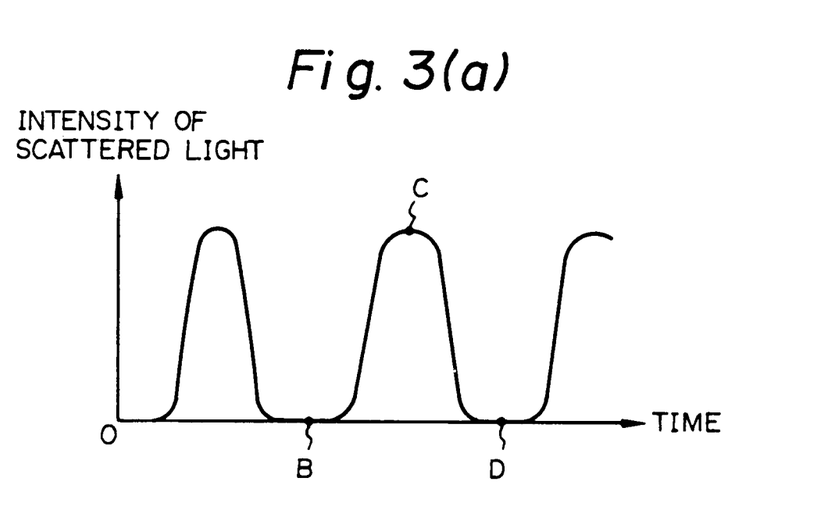
FIG. 3(a) is a characteristic chart showing changes in the intensity of scattered light with time.
Figure 3B:
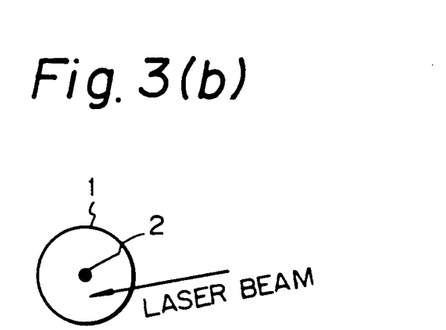
FIGS. 3(b) to 3(d) show the positional relationship between a fine particle and the laser beam at the points B to D in FIG. 3(a)
Figure 3C:
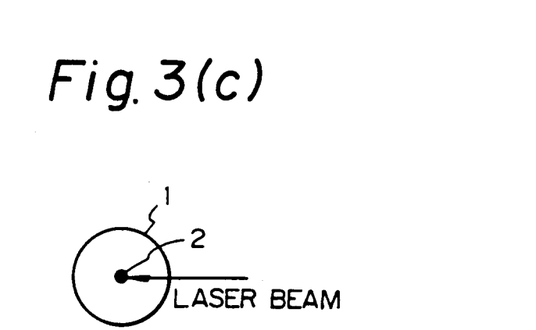
Figure 3D:
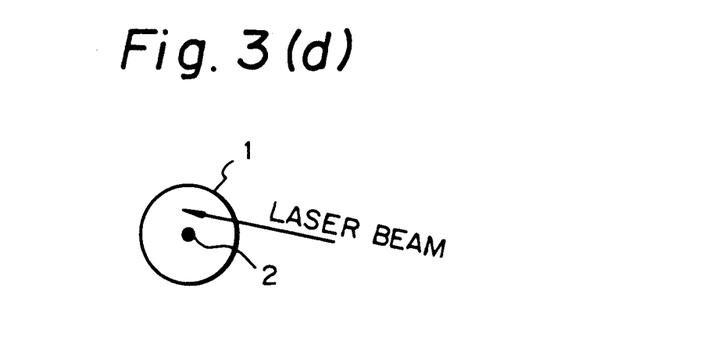

In the foregoing description the measurement of fine particles only, in a very small region on the wafer surface, has been explained. It is, however, possible to measure at least a one-dimensional distribution of fine particles attached to the surface of the wafer 1 by replacing the laser beam scanning mechanism 13 shown in FIG. 1 with a laser beam scanning mechanism comprising a combination of a galvanometer scanner and, for example, either an electrooptic deflector or acoustooptic deflector which employs a signal [shown in FIG. 2(c)] obtained by superposing a minute scanning modulating signal [shown in FIG. 2(a)] on an angular position scanning signal [shown in FIG. 2(b)] which can be regarded as quasi-static in comparison with the modulation and further by providing a controller for the scanning mechanism.

Figure 6:
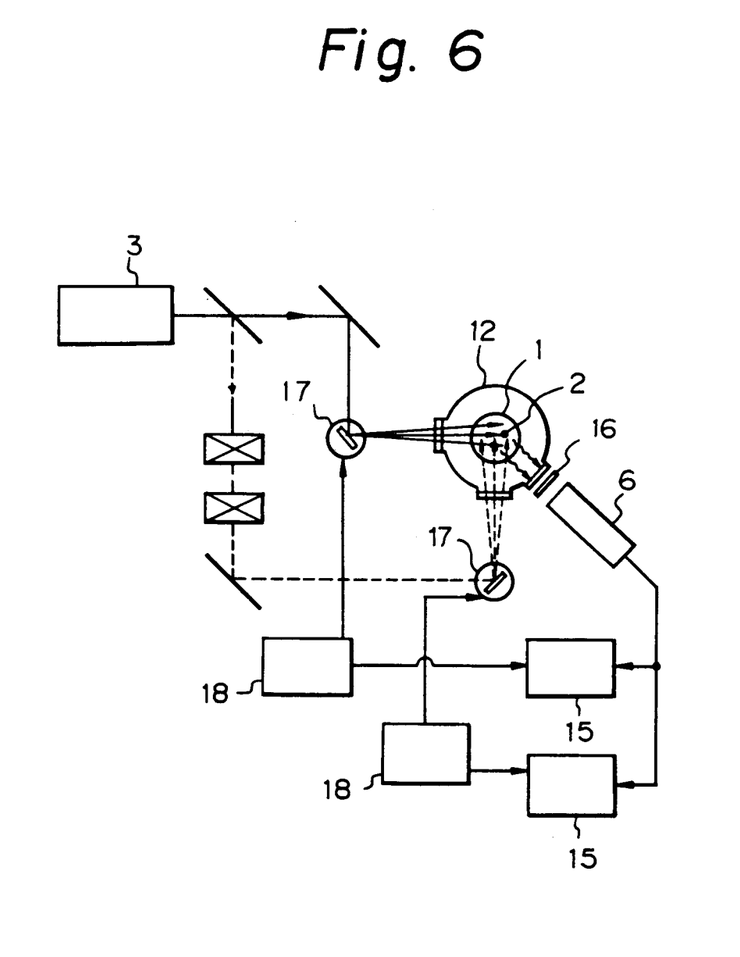
FIG. 6 shows the arrangement of another embodiment of the fine-particle measuring apparatus according to the present invention.

In addition, as shown in FIG. 6, if two sets of laser beam scanning means are provided each comprising a laser beam scanning mechanism 17 and a controller 18 therefore, it is possible to measure a two-dimensional distribution of fine particles 2 on the surface of the wafer 1 with a position resolving power corresponding to the minute scanning with the laser beam.

Although in the foregoing embodiments the present invention has been described with regard to the measurement of fine particles 2 attached to the surface of the wafer 1, the measuring apparatus of the present invention is also capable of measuring fine particles suspended in the space above the wafer surface under conditions where the speed of movement of the fine particles is much lower than the speed of movement of the laser beam which is applied to effect minute scanning.

Although in the first embodiment the laser beam scanning mechanism 13 is constituted by a galvanometer scanner, it is also possible to employ, for example, an electrooptic deflector or an acoustooptic deflector.

Although in the foregoing embodiments the present invention has been described by way of one example in which it is employed to measure fine particles in a process unit, the method that is used in the measuring apparatus of the present invention may, of course, be applied to a measuring apparatus which is designed to perform a measuring operation not related to a process unit.

As has been described above, the fine-paricle measuring apparatus according to the present invention comprises a laser beam scanning mechanism for irradiating a measuring space with a laser beam the angular position of which is minutely modulated at a predetermined frequency, a photodetector which receives light scattered by a fine particle and converts the received light into an electrical signal, and a signal processor which extracts from the electrical signal output by the photodetector a signal component whose frequency is the same as or double that of a modulating signal for the minute scanning with the laser beam and which has a constant phase difference in terms of time with respect to the modulating signal. It is therefore possible to measure with high sensitivity fine particles attached to the surface of a substrate for a semiconductor device which is set in a process unit and fine particles suspended in the space above the substrate surface without substantially disturbing the environment inside the process unit or the process itself.

Further, it is possible to measure at least a one-dimensional distribution of fine particles present in the measuring space by employing a laser beam scanning mechanism which effects scanning with a laser beam the angular position of which is minutely modulated at a predetermined frequency, the laser beam being superposed on a spatial position scanning the speed of which can be regarded as quasi-static in comparison with the modulation.

Although the present invention has been described through specific terms, it should be noted here that the described embodiments are not necessarily exclusive and that various changes and modifications may be imparted thereto without departing from the scope of the invention which is limited solely by the appended claims.

What is claimed is:

1. A fine-particle detecting apparatus for detecting fine particles disposed on the surface of a substrate for a semiconductor device and fine particles suspended in the space above the surface of said substrate by the use of scattering of a laser beam caused by these fine particles, comprising:

a laser beam scanning mechanism for irradiating a measuring space with a laser beam, said mechanism including means for relatively minutely modulating the angular position of the laser beam at a predetermined frequency;

a photodetector which receives light scattered by any of said fine particles and converts the received light into an electrical signal; and a signal processor which extracts from the electrical signal output by said photodetector a signal component whose frequency is an integral multiple of said predetermined frequency for said minute scanning with the laser beam and which has a constant phase difference over time with respect to said predetermined frequency.

2. A fine-particle detecting apparatus according to claim 1, further comprising:

a narrow-band pass multilayer interference filter for limiting a measuring zone containing said fine particles which is disposed in front of said photodetector, said filter having a center transmission wavelength which is the same as the wavelength of said laser beam.

3. A fine-particle detecting apparatus for detecting fine particles disposed on the surface of a substrate for a semiconductor device and fine particles suspended in the space above the surface of said substrate by the use of scattering of a laser beam caused by these fine particles, comprising:

a laser beam scanning mechanism for irradiating a measuring space with a laser beam, said mechanism including means for relatively minutely modulating angular position of the laser beam at a predetermined frequency, said laser beam being furthermore angularly scanned at a speed substantially slower than the modulation;

a photodetector which receives light scattered by any of said fine particles and converts the received light into an electrical signal; and a signal processor which extracts from the electrical signal output by said photodetector a signal component whose frequency is an internal multiple of said predetermined frequency for said minute scanning with the laser beam and which has a constant phase difference over time with respect to said predetermined frequency.

4. A system for detecting a minute particle on or above a semiconductor substrate with a laser beam, comprising:

a laser beam source;

a laser beam scanning mechanism for receiving a laser beam from said laser beam source and scanning said laser beam on a semiconductor substrate, said mechanism including means for generating an oscillation signal to thereby oscillate said laser beam through a given angle, said oscillation signal having a given frequency;

a photodetector for receiving at least a light scattered by a minute particle on or above the semiconductor substrate and providing an electrical output signal; and a signal processor for processing said output signal and extracting a signal component whose frequency is the same as or twice as high as said given frequency of the oscillation signal and whose phase constantly differs from that of said oscillation signal over time.

5. The system of claim 4, further comprising a narrow-band pass multilayer interference filter disposed in front of said photodetector and adapted to define a zone to be inspected, said filter including a center transmission wavelength identical to a wavelength of said laser beam.

6. A minute particle inspection system comprising:

a laser beam source;

first means for receiving a laser beam from said laser beam source and directing said laser beam to a substrate;

second means for providing an oscillation signal to said first means whereby said laser beam is oscillated, said oscillation signal having a given frequency;

third means for receiving at least a light scattered by a minute particle on or above said substrate and providing an electrical output signal; and fourth means for processing said output signal and extracting a signal component whose frequency is identical to or twice as high as said given frequency of the oscillation signal and whose phase constantly differs from that of said oscillation signal.

7. A system for laser scanning a semiconductor substrate, comprising:

a laser beam source;

first means for receiving a laser beam from said laser beam source and directing said laser beam to a semiconductor substrate;

second means for generating an oscillation signal, said oscillation signal having a given frequency;

third means for generating a scan signal, said scan signal having a frequency lower than said given frequency of said oscillation signal;

fourth means for superposing said oscillation signal on said scan signal and providing a superposed signal to said first means whereby said laser beam is scanned on the semiconductor substrate while oscillating back and forth;

fifth means for receiving at least a light scattered by a minute particle on or above the semiconductor substrate and providing an electrical output signal; and sixth means for processing said output signal and extracting a signal component whose frequency is identical to or twice as high as said given frequency of the oscillation signal and whose phase constantly differs from that of said oscillation signal.

* * * * *